United States Patent
Kawakami et al.

(10) Patent No.: US 12,290,501 B2
(45) Date of Patent: May 6, 2025

(54) RIVASTIGMINE-CONTAINING TRANSDERMAL ABSORPTION PREPARATION

(71) Applicant: TEIKOKU SEIYAKU CO., LTD., Kagawa (JP)

(72) Inventors: Satoshi Kawakami, Kagawa (JP); Manabu Sogabe, Kagawa (JP); Taiki Shibata, Kagawa (JP)

(73) Assignee: TEIKOKU SEIYAKU CO., LTD., Kagawa (JP)

( * ) Notice: Subject to any disclaimer, the term of this patent is extended or adjusted under 35 U.S.C. 154(b) by 85 days.

(21) Appl. No.: 16/630,665

(22) PCT Filed: Jul. 12, 2018

(86) PCT No.: PCT/JP2018/026279
§ 371 (c)(1),
(2) Date: Jan. 13, 2020

(87) PCT Pub. No.: WO2019/017266
PCT Pub. Date: Jan. 24, 2019

(65) Prior Publication Data
US 2021/0085633 A1    Mar. 25, 2021

(30) Foreign Application Priority Data
Jul. 19, 2017 (JP) ................. 2017-139954

(51) Int. Cl.
| | | |
|---|---|---|
| A61K 31/27 | (2006.01) | |
| A61K 9/06 | (2006.01) | |
| A61K 47/34 | (2017.01) | |
| A61K 47/38 | (2006.01) | |

(52) U.S. Cl.
CPC ............... *A61K 31/27* (2013.01); *A61K 9/06* (2013.01); *A61K 47/34* (2013.01); *A61K 47/38* (2013.01)

(58) Field of Classification Search
None
See application file for complete search history.

(56) References Cited

U.S. PATENT DOCUMENTS

| | | | | |
|---|---|---|---|---|
| 5,750,136 A | * | 5/1998 | Scholz | A61K 9/006 424/435 |
| 2001/0004494 A1 | * | 6/2001 | Mussig | C09J 123/16 428/343 |
| 2003/0113365 A1 | * | 6/2003 | Schaberg | C09J 133/062 424/449 |
| 2012/0282303 A1 | | 11/2012 | Ito | |
| 2012/0323190 A1 | | 12/2012 | Ito | |
| 2013/0220846 A1 | | 8/2013 | Hiraoka et al. | |
| 2013/0267916 A1 | | 10/2013 | Yu et al. | |
| 2013/0337021 A1 | | 12/2013 | Ito | |
| 2014/0083878 A1 | * | 3/2014 | Tang | A61P 25/28 206/204 |
| 2015/0018782 A1 | | 1/2015 | Hiraoka et al. | |
| 2015/0224063 A1 | | 8/2015 | Ogino et al. | |
| 2015/0374642 A1 | | 12/2015 | Ogino et al. | |
| 2016/0206568 A1 | | 7/2016 | Ogino et al. | |
| 2018/0028464 A1 | | 2/2018 | Komoda et al. | |
| 2018/0289630 A1 | | 10/2018 | Sonobe et al. | |

FOREIGN PATENT DOCUMENTS

| | | |
|---|---|---|
| EP | 3 251 663 | 12/2017 |
| JP | 2014-508728 | 4/2014 |
| JP | 2016-37464 | 3/2016 |
| WO | 2011/074635 | 6/2011 |
| WO | 2011/074636 | 6/2011 |
| WO | 2013/128562 | 9/2013 |
| WO | 2013/187451 | 12/2013 |
| WO | 2016/121805 | 8/2016 |
| WO | 2017/034027 | 3/2017 |
| WO | 2017/073516 | 5/2017 |
| WO | 2018/155682 | 8/2018 |

OTHER PUBLICATIONS

Madan et al. Recent Patents on Drug Delivery & Formulation vol. 9, pp. 95-103. (Year: 2015).*
Extended European Search Report issued Apr. 19, 2021 in European Patent Application No. 18835152.2.
International Search Report issued Sep. 11, 2018 in International (PCT) Application No. PCT/JP2018/026279.
Notice of Reasons for Refusal issued May 17, 2022 in Japanese Patent Application No. 2019-530996, with English translation.
Office Action issued Mar. 4, 2022 in corresponding Taiwanese Patent Application No. 107124748, with English language translation.
Communication pursuant to Article 94(3) EPC issued Jan. 16, 2023 in corresponding European Patent Application No. 18 835 152.2.
Communication pursuant to Article 94(3) EPC issued Sep. 11, 2024 in European Patent Application No. 18 835 152.2.

* cited by examiner

*Primary Examiner* — Katherine Peebles
(74) *Attorney, Agent, or Firm* — Wenderoth, Lind & Ponack, L.L.P.

(57) ABSTRACT

The purpose of the present invention is to provide a rivastigmine-containing transdermal absorption preparation having high adhesion to the skin and capable of continuously administering rivastigmine over a long period of time. A transdermal absorption preparation has rivastigmine, a rubber polymer, a tackifier resin, and a polymer compound having a nitrogen-containing group.

2 Claims, No Drawings

RIVASTIGMINE-CONTAINING TRANSDERMAL ABSORPTION PREPARATION

TECHNICAL FIELD

The present invention relates to a patch containing rivastigmine. More particularly, the present invention relates to a transdermal absorption preparation capable of exhibiting excellent skin adhesion and stable skin permeability of rivastigmine.

BACKGROUND ART

It has been reported that a patient with Alzheimer-type dementia has impairment of the cholinergic nervous system in the brain. On the other hand, it has been known that the cholinergic nervous system in the brain can be activated by increasing acetylcholine in the brain by an inhibitor of acetylcholinesterase or butyrylcholinesterase. Rivastigmine is known as a drug having an inhibitory action against the above-mentioned acetylcholinesterase or butyrylcholinesterase. Rivastigmine can suppress the progression of Alzheimer's dementia symptoms and is therefore used in clinical settings as a medicament for Alzheimer's disease treatment. However, rivastigmine generally causes strong side effects and has been often reported to have side effects such as liver dysfunction and gastrointestinal tract disturbance. In addition, taking of an oral medication itself often becomes difficult for a patient with an advanced symptom. Therefore, a transdermal absorption preparation is suitable for a patient who wants to prevent the development of side effects or who has an advanced symptom.

Currently, EXELON (registered trademark) patch containing rivastigmine is commercially available on the pharmaceutical market. Although for a rivastigmine-containing patch, it is necessary to allow the active ingredient to continuously act over a long period of time, there is a problem of easily peeling off due to a change in body posture or rubbing with clothes during the application of the patch. For this reason, high adhesion to the skin and stable skin permeability of the active ingredient are demanded for the rivastigmine-containing patch.

In view of such circumstances, for example, Patent Document 1 discloses a patch having improved skin adhesiveness while suppressing skin irritation by blending rivastigmine into a patch base containing a thermoplastic elastomer and a non-volatile hydrocarbon oil.

Patent Document 2 discloses a patch having improved skin permeability of rivastigmine while suppressing skin irritation by blending rivastigmine into an adhesive base containing a styrene-isoprene-styrene block copolymer, a tackifier resin, and a plasticizer.

Patent Document 3 discloses a percutaneous absorption preparation comprising an anti-dementia drug, a polymer compound having an amino group, a polyvalent carboxylate ester, a fatty acid alkyl ester, a styrenic polymer compound, and a tackifier resin. It is described that this percutaneous absorption preparation enables efficient transdermal administration of an anti-dementia drug while suppressing skin irritation.

PRIOR ART DOCUMENT

Patent Document

Patent Document 1: WO 2013/187451
Patent Document 2: JP 2014-508728 A
Patent Document 3: WO 2011/074635

DISCLOSURE OF THE INVENTION

Problems to be Solved by the Invention

As described above, various techniques for improvement of the skin adhesion and the skin permeability have been proposed in a transdermal absorption preparation containing rivastigmine, but further improvement is demanded.

For example, Patent Document 1 attempts to control the skin adhesion and suppresses the skin irritation by adding no tackifier resin or a very small amount of 10% by weight or less of a tackifier resin to a patch and by relatively increasing the thickness of an adhesive. Since this patch has a low content of the tackifier resin, the initial adhesive strength is weak, and thus the patch may peel off or partially peel off during the application of the patch and may not show sufficient skin permeability of the drug.

In Patent Document 2, the adhesiveness of the patch to the skin has not been studied.

In Patent Document 3, the formulation is designed for donepezil, which is basically solid at normal temperature and is an anti-dementia drug having poor transdermal absorbability. The formulation contains various liquid components such as triethyl citrate and isopropyl myristate for improving transdermal absorbability. Therefore, if rivastigmine, which is liquid at normal temperature, is used instead of solid donepezil, it is considered that the drug-containing layer is too soft to maintain the physical properties such as adhesion of the preparation.

The present invention has been made in view of the above circumstances, and an object of the present invention is to provide a rivastigmine-containing transdermal absorption preparation having high adhesion to the skin and capable of continuously administering rivastigmine over a long period of time.

Means for Solving the Problems

That is, the present invention has the following configurations.

[1] A transdermal absorption preparation comprising rivastigmine, a rubber polymer, a tackifier resin, and a polymer compound having a nitrogen-containing group.

[2] The transdermal absorption preparation according to [1], wherein the nitrogen-containing group is one or more selected from the group consisting of primary, secondary, or tertiary amino groups, imino groups, imide groups, amide groups, and quaternary ammonium groups.

[3] The transdermal absorption preparation according to [1] or [2], wherein the polymer compound having the nitrogen-containing group is a polymer of a (meth)acrylic monomer having the nitrogen-containing group or a vinyl monomer having the nitrogen-containing group, a copolymer of these monomers, a copolymer of at least one of the monomers and a (meth)acrylic monomer having no nitrogen-containing group, or a condensate of polyvinyl alcohol and mono- or dialkylamino acetate.

[4] The transdermal absorption preparation according to [1], wherein the polymer compound having the nitrogen-containing group is aminoalkyl methacrylate copolymer E.

[5] The transdermal absorption preparation according to any of [1] to [4], wherein the rubber polymer is one or more selected from the group consisting of styrene-isoprene-styrene block copolymers, styrene-butadiene-styrene block copolymers, styrene-ethylene-butylene-styrene block copolymers, styrene-isoprene rubbers, polyisoprene rubbers, styrene-butadiene rubbers, chloroprene rubbers, liquid rubbers, natural rubber latexes, synthetic latexes, polybutene, polyisoprene, polybutylene, and polyisobutylene.

[6] The transdermal absorption preparation according to any of [1] to [5], further comprising a cellulose derivative.

[7] The transdermal absorption preparation according to [6], wherein the cellulose derivative is one or more selected from the group consisting of carboxymethyl cellulose, carmellose sodium, methyl cellulose, ethyl cellulose, hydroxyethyl cellulose, hydroxypropyl cellulose, and hydroxypropyl methyl cellulose.

[8] The transdermal absorption preparation according to any of [1] to [7], wherein a content of the rivastigmine in the transdermal absorption preparation is 5 mass % or more and 30 mass % or less.

[9] The transdermal absorption preparation according to any of [1] to [8], wherein a content of the polymer compound having the nitrogen-containing group in the transdermal absorption preparation is 1 mass % or more and 20 mass % or less.

[10] The transdermal absorption preparation according to any of [1] to [9], wherein a mass ratio of the content of the polymer compound having the nitrogen-containing group to the content of the rivastigmine is 0.05 or more and 4 or less.

Effects of the Invention

According to the present invention, by the above-described configuration, it is possible to provide a rivastigmine-containing transdermal absorption preparation having high adhesion to the skin and capable of continuously administering rivastigmine over a long period of time.

MODE FOR CARRYING OUT THE INVENTION

The inventors considered that, on providing the rivastigmine-containing transdermal absorption preparation capable of achieving the above-mentioned object, it is necessary to take the drug properties of rivastigmine shown in the following (i) to (iii) into account:
(i) rivastigmine acts as a plasticizer in the preparation since rivastigmine is liquid at normal temperature;
(ii) when administering rivastigmine in an amount necessary for treatment by an application of the preparation to a human once a day, it is necessary to blend a relatively high concentration of rivastigmine per one sheet of the preparation; and
(iii) rivastigmine is a drug with high transdermal absorbability, and during the application of the preparation to a patient, a relatively large amount of the drug is absorbed into the body of the patient with time, whereby the difference in the drug content in the preparation between immediately after the application and immediately before peeling is very large.

For the above reasons (i) and (ii), when the preparation before the application contains a large amount of rivastigmine, the preparation is in a state of containing a large amount of plasticizer, resulting in having high skin adhesion at that time. However, for the above reason (iii), the content of rivastigmine decreases rapidly after the application of the preparation to the skin, so that the content of the entire plasticizing components in the preparation decreases and the skin adhesion deteriorates. As a result, peeling of the preparation easily occurs and the transdermal absorbability of the drug decreases. In order to avoid these problems, an increase in the initial content of plasticizers other than rivastigmine can be considered. However, this countermeasure entails deterioration in the initial physical properties of the preparation, and the skin adhesion contrarily decreases.

Based on such characteristics of rivastigmine, the inventors have conducted intensive studies and found that by blending a polymer compound having a nitrogen-containing group into an adhesive base containing rivastigmine, a rubber polymer, and a tackifier resin, a transdermal absorption preparation having high adhesion to the skin and capable of continuously administering rivastigmine over a long period of time can be obtained. The inventors accomplished the invention based on this finding.

Hereinafter, the components constituting the preparation of the present invention will be described in detail.

Rivastigmine, which is the main drug component of the transdermal absorption preparation of the present invention, is an active ingredient and also acts as a plasticizer because rivastigmine is liquid at normal temperature. This plasticizing action can improve the adhesion during the application of the preparation, so that a stable drug supply capability can be easily exhibited. To that end, the content of rivastigmine needs to be controlled in consideration of both the drug efficacy and the physical properties of the preparation. The content of rivastigmine (the value in terms of rivastigmine in the case of rivastigmine salt) is grasped as % when the total amount of the adhesive layer is 100 mass %. The content of rivastigmine is preferably 5 mass % or more and 30 mass % or less. If the content of rivastigmine is less than 5 mass %, a desired drug efficacy cannot be obtained, and in addition, the initial plasticizing action of rivastigmine is weakened and the skin adhesion decreases, so that there may be caused influences such as peeling and falling off of the preparation during application. Therefore, the content of rivastigmine is preferably 5 mass % or more, more preferably 10 mass % or more, and further preferably 12 mass % or more. On the other hand, if the content of rivastigmine exceeds 30 mass %, the initial plasticizing action becomes too high, and the physical properties such as adhesion of the patch may decrease. Therefore, the content of rivastigmine is preferably 30 mass % or less, more preferably 20 mass % or less, and further preferably 15 mass % or less.

Rivastigmine is preferably blended in a free form (free-type), and may be blended as a salt as necessary. The salt is not limited as long as it is a pharmaceutically acceptable salt. As examples of such salt, acid addition salt with a medically acceptable inorganic or organic acid such as hydrochloride, acetic acid salt, tartrate, oxalate, citrate, or the like can be given.

A rubber polymer has a shape retention property and enhances an adhesion between the preparation and the skin. As a result, the rubber polymer can enhance the transdermal absorbability of rivastigmine. Examples of the rubber polymer include one or more selected from the group consisting of styrene-isoprene-styrene block copolymers (SIS), styrene-butadiene-styrene block copolymers (SBS), styrene-ethylene-butylene-styrene block copolymers (SEBS), styrene-isoprene rubbers, polyisoprene rubbers, styrene-butadiene rubbers, chloroprene rubbers, liquid rubbers, natural rubber latexes, synthetic latexes (SBR synthetic latexes, etc.), polybutene, polyisoprene, polybutylene, and polyisobutylene. Examples of the liquid rubbers include liquid polyisoprene rubbers, liquid polybutadiene rubbers, and liquid polystyrene butadiene rubbers, which are liquid at normal temperature. These may be used singly or in combination of two or more. Among these, one or more selected from the group consisting of SIS, polybutylene, polyisobutylene, polyisoprene rubbers, and liquid polyisoprene rubbers are preferable, and one or more selected from the group consisting of SIS, polyisoprene rubbers, and liquid polyisoprene rubbers are more preferable.

The content (the sole content when contained singly, and the total amount when contained in combination of two or more) of the rubber polymer is preferably 10 mass % or more and 60 mass % or less when the total amount of the adhesive layer is 100 mass %. If the content of the rubber polymer is less than 10 mass %, the formation of an adhesive layer may become difficult, or sufficient skin permeability may not be obtained. Therefore, the content of the rubber polymer is preferably 10 mass % or more, more preferably 20 mass % or more, and further preferably 30 mass % or more. On the other hand, by setting the content of the rubber polymer to 60 mass % or less, the content of the tackifier resin can be increased, so that the adhesion to the skin can be improved. Therefore, the content of the rubber polymer is preferably 60 mass % or less, more preferably 55 mass % or less, and further preferably 40 mass % or less.

The tackifier resin is not particularly limited as long as it can impart adhesive strength to the preparation. For example, the tackifier resin is preferably one or more selected from the group consisting of alicyclic saturated hydrocarbon resins, aliphatic hydrocarbon resins, terpene resins, rosin, rosin derivatives, xylene resins, phenol resins, and maleic resins. These can be used singly or in combination of two or more. Considering the initial adhesive strength of the preparation and the compatibility with rivastigmine, the tackifier resin is more preferably one or more selected from the group consisting of rosin derivatives and alicyclic saturated hydrocarbon resins. Examples of the alicyclic saturated hydrocarbon resins include ARKON P70, ARKON P90, ARKON P100, ARKON P115, and ARKON P125 manufactured by Arakawa Chemical Industries, Ltd. Examples of the aliphatic hydrocarbon resins include Quintone B170 manufactured by Zeon Corporation and Escorez 1202 manufactured by Tonex Co., Ltd. Examples of the terpene resins include Clearon P-125 manufactured by Yasuhara Chemical Co., Ltd. Examples of the rosin derivatives include rosin glycerol ester, hydrogenated rosin, hydrogenated rosin glycerol ester, and pentaerythritol ester of rosin. Examples of the xylene resins include xylene-formaldehyde resin, which is a reaction product of xylene and formaldehyde. Examples of the phenol resins include phenol-xylene-formaldehyde resin.

The content (the sole content when contained singly, and the total amount when contained in combination of two or more) of the tackifier resin is preferably 30 mass % or more and 70 mass % or less when the total amount of the adhesive layer is 100 mass %. If the content of the tackifier resin is less than 30 mass %, the adhesion to the skin decreases, so that the preparation may peel and fall off during application. The content of the tackifier resin is more preferably 40 mass % or more, and further preferably 45 mass % or more. On the other hand, if the content of the tackifier resin exceeds 70 mass %, the preparation becomes too hard and a desired skin adhesion may not be obtained. The content of the tackifier resin is more preferably 60 mass % or less, and further preferably 55 mass % or less.

The polymer compound having a nitrogen-containing group functions as an adhesion enhancer in the transdermal absorption preparation of the present invention. Examples of the polymer compound having a nitrogen-containing group include a polymer of a (meth)acrylic monomer having a nitrogen-containing group or a vinyl monomer having a nitrogen-containing group, a copolymer of these monomers, a copolymer of at least one of the above monomers and a (meth)acrylic monomer having no nitrogen-containing group, or a condensate of polyvinyl alcohol and mono- or dialkylamino acetate.

Examples of the nitrogen-containing group include one or more selected from the group consisting of primary, secondary, or tertiary amino groups, imino groups, imide groups, amide groups, and quaternary ammonium groups.

As the (meth)acrylic monomer having a nitrogen-containing group, an alkylaminoalkyl (meth)acrylate can be mentioned. Examples of the alkylaminoalkyl (meth)acrylate include one or more selected from the group consisting of monoalkylaminoalkyl (meth)acrylates, dialkylaminoalkyl (meth)acrylates, and trialkylaminoalkyl (meth)acrylates. These may be used singly or in combination of two or more.

Examples of the monoalkylaminoalkyl (meth)acrylates include one or more selected from the group consisting of monomethylaminoethyl (meth)acrylate, monoethylaminoethyl (meth)acrylate, monomethylaminopropyl (meth)acrylate, and monoethylaminopropyl (meth)acrylate.

Examples of the dialkylaminoalkyl (meth)acrylates include one or more selected from the group consisting of dimethylaminoethyl (meth)acrylate, dimethylaminomethyl (meth)acrylate, diethylaminomethyl (meth)acrylate, diethylaminoethyl (meth)acrylate, dimethylaminopropyl (meth)acrylate, diethylaminopropyl (meth)acrylate, dipropylaminoethyl (meth)acrylate, and dipropylaminomethyl (meth)acrylate.

Examples of the trialkylaminoalkyl (meth)acrylates include trimethylaminoethyl (meth)acrylate.

As the vinyl monomer having a nitrogen-containing group, a vinylamine monomer can be mentioned. Examples of the vinylamine monomer include one or more selected from the group consisting of N-vinylpyrrolidone, N-vinylpyrazine, N-vinylimidazole, N-vinyloxazole, N-vinylmorpholine, N-vinylpyrazole, N-vinylisoxazole, N-vinylthiazole, N-vinylisothiazole, N-vinylpyridazine, N-vinylpyridine, N-vinylpyrimidine, N-vinylpiperazine, and N-vinylpyrrole.

Examples of the (meth)acrylic monomer having no nitrogen-containing group include one or more selected from the group consisting of methyl acrylate, propyl acrylate, butyl acrylate, isobutyl acrylate, hexyl acrylate, octyl acrylate, 2-ethylhexyl acrylate, decyl acrylate, isodecyl acrylate, lauryl acrylate, stearyl acrylate, 2-hydroxyethyl acrylate, hydroxypropyl acrylate, methyl methacrylate, ethyl methacrylate, decyl methacrylate, butyl methacrylate, isobutyl methacrylate, 2-ethylhexyl methacrylate, isodecyl methacrylate, lauryl methacrylate, stearyl methacrylate, 2-hydroxyethyl methacrylate, and hydroxypropyl methacrylate. Among these, one or more selected from the group consisting of methyl methacrylate and butyl methacrylate are preferred.

As the condensate of polyvinyl alcohol and an alkylamino acetate, a polyvinyl acetal dialkylamino acetate can be mentioned. Examples of the polyvinyl acetal dialkylamino acetate include one or more selected from the group consisting of polyvinyl acetal dimethylamino acetate, polyvinyl acetal diethylamino acetate, and polyvinyl acetal dibutylamino acetate.

As the polymer compound having a nitrogen-containing group of the present invention, a copolymer of a (meth)acrylic monomer having a nitrogen-containing group and a (meth)acrylic monomer having no nitrogen-containing group is preferred because of high compatibility with rivastigmine. As such a copolymer, a methyl methacrylate-butyl methacrylate-dimethylaminoethyl methacrylate copolymer, which is a copolymer of methyl methacrylate, butyl methacrylate and dimethylaminoethyl methacrylate, is more preferred. As example of the methyl methacrylate-butyl methacrylate-dimethylaminoethyl methacrylate copolymer, aminoalkyl methacrylate copolymer E [EUDRAGIT (registered trademark) EPO (manufactured by Evonik)] can be mentioned. Aminoalkyl methacrylate copolymer E is solid at normal temperature and is a polymer conventionally used as a coating agent or binder. However, as shown in Examples described later, it is a finding first found by the inventors that aminoalkyl methacrylate copolymer E functions as an excellent adhesion enhancer when mixed with rivastigmine.

The content (the sole content when contained singly, and the total amount when contained in combination of two or more) of the polymer compound having a nitrogen-containing group is preferably 1 mass % or more and 20 mass % or less when the total amount of the adhesive layer is 100 mass %. If the content is less than 1 mass %, a desired skin adhesion may not be obtained. The content is more preferably 3 mass % or more, and further preferably 5 mass % or more. On the other hand, if the content of the polymer compound having a nitrogen-containing group exceeds 20 mass %, the physical properties of the preparation is destroyed, and the skin adhesion may decrease. The content is more preferably 15 mass % or less, and further preferably 10 mass % or less.

The mass ratio of the content of the polymer compound having a nitrogen-containing group to the content of rivastigmine (the content of the compound having a nitrogen-containing group/the content of rivastigmine) is preferably 0.05 or more and 4 or less. If the mass ratio is less than 0.05, it is difficult to obtain a desired skin adhesion. Therefore, the mass ratio is preferably 0.05 or more, more preferably 0.1 or more, and further preferably 0.2 or more. On the other hand, if the mass ratio exceeds 4, the physical properties of the preparation may decrease, and the skin adhesion may contrarily decrease. Therefore, the mass ratio is preferably 4 or less, more preferably 2 or less, and further preferably 1.0 or less.

Preferably, the transdermal absorption preparation of the present invention may further contain a cellulose derivative. A cellulose derivative is a hygroscopic compound and is sometimes added to a plaster agent for the purpose of preventing the peeling of the preparation due to perspiration or the like. When the cellulose derivative was added to an adhesive base containing rivastigmine, a rubber polymer, and a tackifier resin, the dispersibility of the cellulose derivative deteriorated. However, surprisingly, it was found that when a hygroscopic compound together with the polymer compound having a nitrogen-containing group are included in the preparation, the dispersibility of the cellulose derivative is improved, and as a result, the skin adhesion can be improved. Such finding was found by the inventors for the first time.

The cellulose derivative is preferably one or more selected from the group consisting of carboxymethyl cellulose, carmellose sodium, methyl cellulose, ethyl cellulose, hydroxyethyl cellulose, hydroxypropyl cellulose, and hydroxypropyl methyl cellulose. Among these, one or more selected from the group consisting of hydroxypropyl methyl cellulose and hydroxypropyl cellulose are more preferable, and hydroxypropyl methyl cellulose is further preferable.

The content (the sole content when contained singly, and the total amount when contained in combination of two or more) of the cellulose derivative is preferably 0.1 mass % or more and 6 mass % or less when the total amount of the adhesive layer is 100 mass %. If the content is 0.1 mass % or more, the skin adhesion can be easily improved. The content is preferably 0.1 mass % or more, more preferably 0.3 mass % or more, and further preferably 0.5 mass % or more. On the other hand, if the content of the cellulose derivative exceeds 6 mass %, the dispersibility of the cellulose derivative is deteriorated and it is difficult to improve the skin adhesion. The content is preferably 6 mass % or less, more preferably 4 mass % or less, and further preferably 3 mass % or less.

When additives described below are added, each of the contents of the above mentioned rivastigmine, rubber polymer, tackifier resin, polymer compound having a nitrogen-containing group, and cellulose derivative should be construed as % (mass %) with respect to the entire adhesive layer including the additives (not including a backing and a release layer).

In addition to the above-mentioned components, the preparation of the present invention may contain additives that are usually used in transdermal absorption preparations, as necessary, within a range that does not impair the effect of the invention.

For example, a liquid component can be blended as a softening agent to the extent that the component does not affect the physical properties of the preparation. Examples of the liquid component include one or more selected from the group consisting of petroleum oils such as naphthenic process oils and aromatic process oils; squalane; squalene; vegetable oils such as olive oil, camellia oil, castor oil, tall oil, peanut oil; synthetic oils such as silicone oil; liquid fatty acid esters such as oleyl oleate, isopropyl myristate, hexyl laurate, diethyl sebacate, diisopropyl sebacate; diethylene glycol; polyethylene glycol; glycol salicylate; propylene glycol; dipropylene glycol; triacetin; triethyl citrate; crotamiton; dibasic acid esters such as dibutyl phthalate and dioctyl phthalate; glycerol; and liquid higher alcohols such as isostearyl alcohol, octyldodecanol, and oleyl alcohol. These can be used singly or in combination of two or more.

When blending the liquid component (softening agent), for example, the content (the sole content when contained singly, and the total amount when contained in combination of two or more) of the softening agent is preferably more than 0 mass % and less than 5 mass % when the total amount of the adhesive layer is 100 mass %. Thereby, the adhesive strength can be easily improved while suppressing skin irritation caused by the softening agent. From such a viewpoint, the content of the softening agent is more preferably 0.1 mass % or more and 4 mass % or less, and further preferably 0.2 mass % or more and 3 mass % or less.

In addition, an antioxidant, a filler, a water-soluble polymer, a crosslinking agent, a preservative, and a UV absorber may be blended as necessary.

Examples of the antioxidant include one or more selected from the group consisting of tocopherols and ester derivatives thereof, ascorbic acid, ascorbyl stearate, nordihydroguaiaretic acid, dibutylhydroxytoluene (hereinafter abbreviated as "BHT"), and butylhydroxyanisole.

Examples of the filler include one or more selected from the group consisting of calcium carbonate, magnesium carbonate, silicates such as aluminum silicate and magnesium silicate, silicic acid, barium sulfate, calcium sulfate, calcium zincate, zinc oxide, titanium oxide, and silicon dioxide.

Examples of the water-soluble polymer include one or more selected from the group consisting of casein, dextran, sodium alginate, dextrin, polyvinyl alcohol, polyacrylic acid, polyacrylamide, sodium polyacrylate, polyvinylpyrrolidone, and carboxyvinyl polymer.

Examples of the crosslinking agent include one or more selected from the group consisting of thermosetting resins such as amino resin, phenol resin, epoxy resin, alkyd resin, and unsaturated polyester; isocyanate compounds; blocked isocyanate compounds; organic crosslinking agents; and inorganic crosslinking agents such as metal or metal compounds.

Examples of the preservative include one or more selected from the group consisting of ethyl parahydroxybenzoate, propyl parahydroxybenzoate, and butyl parahydroxybenzoate.

Examples of the UV absorber include one or more selected from the group consisting of p-aminobenzoic acid derivatives, anthranilic acid derivatives, salicylic acid derivatives, amino acid compounds, dioxane derivatives, coumarin derivatives, imidazoline derivatives, and pyrimidine derivatives.

In addition, esters (such as cetyl lactate) that are solid at normal temperature, purified lanolin, cholesterol, gum arabic, and lecithin may be blended.

The thickness of the adhesive layer (the layer containing the active ingredient, the rubber polymer, the tackifier resin, and the polymer compound having a nitrogen-containing group, and further containing, as necessary, the cellulose derivative or other additives) is preferably 30 μm or more and 200 μm or less. If the thickness of the adhesive layer is less than 30 μm, the sustainability of drug release may be decreased. The thickness of the adhesive layer is preferably 30 μm or more, and more preferably 50 μm or more. On the other hand, if the thickness of the adhesive layer exceeds 200 μm, not only the cost increases, but also the amount of drug per unit area in the adhesive layer increases, and as a result, the drug concentration after the lapse of time does not decrease significantly compared with the drug concentration at the initial stage of application, so that the skin irritation at the time of peeling may increase. The thickness of the adhesive layer is preferably 200 μm or less, and more preferably 150 μm or less.

The transdermal absorption preparation of the present invention is preferably a transdermal absorption patch preparation comprising a backing layer, an adhesive layer, and a release layer. Although the above description is made assuming that the patch is a matrix type patch, the transdermal absorption preparation of the present invention is not limited to this.

As the backing, a stretchable or non-stretchable backing can be used. Examples of the backing include fabric, non-woven fabric, polyurethane, polyester, polyvinyl acetate, polyvinylidene chloride, polyethylene, polyethylene terephthalate (hereinafter abbreviated as "PET"), aluminum sheet, and a composite material of these examples.

The release layer is not particularly limited as long as the release layer protects the adhesive layer and prevents rivastigmine contained in the adhesive layer from being altered until the transdermal absorption preparation is applied on the skin, and as long as the release layer is silicon-coated so as to be easily peeled off. Examples of the release layer include silicon-coated polyethylene film, silicon-coated polyethylene terephthalate film, and silicon-coated polypropylene film.

The transdermal absorption preparation of the present invention can be produced by any method, for example, shown as follows: a method in which a drug-containing base composition is heated to dissolve, the dissolved base composition is applied to a release layer or a backing, and then the resultant object is bonded to a backing or a release film to obtain a preparation (hot-melt method), and a method in which a drug-containing base component is dissolved in a solvent such as toluene, hexane, and ethyl acetate, the resultant mixture is extended over a release layer or a backing, the solvent is removed by drying, and then the resultant object is laminating on a backing or a release layer (solvent method).

The present application claims the benefit of priority based on Japanese Patent Application No. 2017-139954 filed on Jul. 19, 2017. The entire contents of the specification of Japanese Patent Application No. 2017-139954 filed on Jul. 19, 2017 are incorporated herein by reference.

EXAMPLES

Hereinafter, the present invention will be described in further detail with reference to examples below. It should be noted, however, that the present invention is not limited to the following examples, and the variation and the modification of the present invention without departing the gist described above and below are all included the technical scope of the present invention.

Example 1

19 g of styrene-isoprene-styrene block copolymer, 14 g of liquid polyisoprene rubber, 33 g of alicyclic saturated hydrocarbon resin (ARKON P100), and 17 g of hydrogenated rosin glycerol ester were mixed and dissolved in a suitable amount of toluene to obtain an adhesive base solution. 5 g of aminoalkyl methacrylate copolymer E was dissolved in 12 g of rivastigmine, the adhesive base solution was then added thereto, and the resultant mixture was stirred and mixed to obtain a homogenous adhesive solution. The obtained adhesive solution was spread on a release layer (PET film), and then the solvent was dried and removed to form an adhesive layer with a thickness of 150 μm. Next, a backing (PET film) was bonded to the adhesive layer to obtain a patch. The content of each component was shown in Table 1.

Examples 2 to 7

Each of the patches of Examples 2 to 7 was obtained by the same production method as in Example 1 except that hydroxypropyl methyl cellulose was added together with the adhesive base solution, the content of each component was changed as shown in Table 1, and the thickness of the adhesive layer was changed to the thickness shown in Table 1.

Comparative Example 1

The patch of Comparative Example 1 was obtained by the same production method as in Example 1 except that aminoalkyl methacrylate copolymer E was not added, and the content of each component was changed as shown in Table 1.

Comparative Example 2

The patch of Comparative Example 2 was obtained by the same production method as in Example 5 except that 2-ethylhexyl acrylate-vinyl acetate-2-hydroxyethyl acrylate copolymer (DURO-TAK 87-4287), which is an acrylic adhesive agent, was used instead of aminoalkyl methacrylate copolymer E.

Comparative Example 3

The patch of Comparative Example 3 was obtained by the same production method as in Example 5 except that butyl methacrylate-methyl methacrylate copolymer (PLASTOID B), which is an excipient, was used instead of aminoalkyl methacrylate copolymer E. Like aminoalkyl methacrylate copolymer E, Plastoid B is solid at normal temperature and is one of polymers used as a coating agent or a binder.

Comparative Example 5

15 g of styrene-isoprene-styrene block copolymer and 28 g of liquid paraffin were mixed and dissolved in a suitable amount of toluene to obtain an adhesive base solution. 7 g of rivastigmine was added to the adhesive base solution, and the resultant mixture was stirred and mixed to obtain a homogenous adhesive solution. The obtained adhesive solution was spread on a release layer (PET film), and then the solvent was dried and removed to form an adhesive layer with a thickness of 128.6 μm such that the content of rivastigmine in the adhesive layer after drying was 1.8 mg/cm$^2$. Next, a backing (PET film) was bonded to the adhesive layer to obtain a patch of Comparative Example 5. Comparative Example 5 was produced with reference to Example 3 of Patent Document 1 (WO 2013/187451).

Comparative Example 6

19.5 g of styrene-isoprene-styrene block copolymer, 18 g of alicyclic saturated hydrocarbon resin (ARKON P100), and 5.5 g of polybutene were mixed and dissolved in a suitable amount of toluene to obtain an adhesive base solution. The adhesive base solution was added to 7 g of rivastigmine, and the resultant mixture was stirred and mixed to obtain a homogenous adhesive solution. The obtained adhesive solution was spread on a release layer (PET film), and then the solvent was dried and removed to form an adhesive layer with a thickness of 85 μm such that the content of rivastigmine in the adhesive layer after drying was 1.2 mg/cm$^2$. Next, a backing (PET film) was bonded to the adhesive layer to obtain a patch of Comparative Example 6. Comparative Example 6 was produced with reference to Example 1 of Patent Document 2 (JP 2014-508728 A).

Adhesion Test: Probe Tack Test

In order to compare the adhesions of Examples 1 to 7 and Comparative Examples 1 to 3, 5, and 6, a probe tack test was performed. First, a test preparation was prepared by cutting the preparation of each of the Examples and the Comparative Examples into a circle with a diameter of 14 mm. Next, a double-sided tape was affixed on a sample stage of a rheometer, and the test preparation was affixed on the sample stage with the PET film facing upward. Then, after attaching a stainless steel disk-shaped probe (diameter: 5 mm) to a pressure-sensitive shaft attachment, the PET film was peeled from the test preparation, and the sample stage was raised at a rate of 10 mm/min. Finally, the adhesive surface was brought into contact with the probe with a force of 50 g and left still for 10 seconds, and then a force required to pull the adhesive surface apart was measured to obtain a tack force (g). The results are shown in Table 1.

Finger Tack Test (Sensory Evaluation)

In order to sensorially evaluate the tackiness of each of Examples 1 to 7 and Comparative Examples 1 to 3, 5, and 6, a finger tack test was performed. Specifically, a finger was pressed against a surface of the adhesive layer, and tackiness (adhesive strength) when the finger was pulled apart was evaluated. The patches having a high adhesive strength were evaluated as being excellent (○), the patches having a medium adhesive strength were evaluated as being good (Δ), and the patches having a low adhesive strength were evaluated as being poor (×). The results are shown in Table 1.

TABLE 1

| | | | Example 1 | Example 2 | Example 3 | Example 4 | Example 5 | Example 6 | Example 7 |
|---|---|---|---|---|---|---|---|---|---|
| Main drug | Rivastigmine | mass % | 12 | 12 | 12 | 13 | 13 | 13 | 13 |
| Rubber polymer | Styrene-isoprene-styrene block copolymer | mass % | 19 | 18.5 | 20 | 19.2 | 19 | 18.7 | 18.4 |
| | Liquid polyisoprene rubber | mass % | 14 | 14 | 13.5 | 13 | 13 | 13 | 13 |
| | Polybutene | mass % | — | — | — | — | — | — | — |
| Tackifier resin | Alicyclic saturated hydrocarbon resin | mass % | 33 | 33.3 | 26 | 32.2 | 32 | 31.5 | 31.1 |
| | Hydrogenated rosin glycerol ester | mass % | 17 | 16.7 | 18 | 17.1 | 17 | 16.8 | 16.5 |
| Aminoalkyl methacrylate copolymer E | | mass % | 5 | 5 | 10 | 5 | 5 | 5 | 5 |
| 2-ethylhexyl acrylate-vinyl acetate-2-hydroxyethyl acrylate copolymer (Duro-tak 87-4287) | | mass % | — | — | — | — | — | — | — |
| Butyl methacrylate-methyl methacrylate copolymer (Plastoid B) | | mass % | — | — | — | — | — | — | — |
| Hydroxypropyl methyl cellulose | | mass % | — | 0.5 | 0.5 | 0.5 | 1 | 2 | 3 |
| Liquid Paraffin | | mass % | — | — | — | — | — | — | — |
| Thickness of the adhesive layer | | (μm) | 150 | 150 | 150 | 138.5 | 138.5 | 138.5 | 138.5 |
| Tack force | | (g) | 662 | 687.5 | 705.8 | 721.8 | 850.5 | 708.2 | 718.7 |
| Finger Tack Test results | | | Δ | ○ | ○ | ○ | ○ | ○ | ○ |

| | | | Comparative Example 1 | Comparative Example 2 | Comparative Example 3 | Comparative Example 5 | Comparative Example 6 |
|---|---|---|---|---|---|---|---|
| Main drug | Rivastigmine | mass % | 12 | 13 | 13 | 14 | 14 |
| Rubber polymer | Styrene-isoprene-styrene block copolymer | mass % | 20 | 19 | 19 | 30 | 39 |
| | Liquid polyisoprene rubber | mass % | 14 | 13 | 13 | — | — |
| | Polybutene | mass % | — | — | — | — | 11 |
| Tackifier resin | Alicyclic saturated hydrocarbon resin | mass % | 36 | 32 | 32 | — | 36 |
| | Hydrogenated rosin glycerol ester | mass % | 18 | 17 | 17 | — | — |

TABLE 1-continued

| | | | | | | |
|---|---|---|---|---|---|---|
| Aminoalkyl methacrylate copolymer E | mass % | — | — | — | — | — |
| 2-ethylhexyl acrylate-vinyl acetate-2-hydroxyethyl acrylate copolymer (Duro-tak 87-4287) | mass % | — | 5 | — | — | — |
| Butyl methacrylate-methyl methacrylate copolymer (Plastoid B) | mass % | — | — | 5 | — | — |
| Hydroxypropyl methyl cellulose | mass % | — | 1 | 1 | — | — |
| Liquid Paraffin | mass % | — | — | — | 56 | — |
| Thickness of the adhesive layer | (μm) | 150 | 138.5 | 138.5 | 128.6 | 85 |
| Tack force | (g) | 445.9 | 353.4 | 373.5 | 162.3 | 495.7 |
| Finger Tack Test results | | x | x | x | x | Δ |

The following can be considered from Table 1.

Example 1, which satisfies the requirements of the present invention, had a higher tack force than the tack forces of Comparative Examples 1 to 3, 5, and 6. Furthermore, in Examples 2 to 7, due to the addition of hydroxypropyl methyl cellulose, the synergistic effect of hydroxypropyl methyl cellulose and aminoalkyl methacrylate copolymer E was exhibited, the tack force was further increased, and excellent results were also obtained in the finger tack test. From this fact, it is considered that the preparation of the present invention has excellent skin adhesion.

In Vitro Skin Permeability Test

To examine the transdermal absorbability of rivastigmine in each of Example 5 and Comparative Example 4 (commercially available rivastigmine-containing patch (EXELON (registered trademark) patch)), an in vitro skin permeability test was performed. First, an excised dorsal skin of a white male was treated so as to have a thickness of 750 μm, and then put on a Franz diffusion cell. Each preparation cut in a round shape with a diameter of 14 mm was applied to this skin. The receptor side was filled with phosphate buffered saline (pH 7.5), and warm water of 37° C. was circulated in the water jacket. The receptor solution was sampled with time, the amount of rivastigmine that permeated the skin was measured by a liquid chromatography. From the measurement results, the cumulative drug permeation amount ($\mu g/cm^2$) after 24 hours from the start of the test and the maximum value of a drug absorption rate (flux: $\mu g/cm^2/hour$) were calculated. The results are shown in Table 2.

TABLE 2

| | Cumulative drug permeation amount after 24 hours from the start of the test ($\mu g/cm^2$) | Maximum value of a drug absorption rate ($\mu g/cm^2/hour$) |
|---|---|---|
| Example 5 | 789.2 | 50.4 |
| Comparative Example 4 | 737.8 | 50.4 |

The following can be considered from Table 2.

Example 5, which satisfies the requirements of the present invention, as compared with Comparative Example 4 (commercially available rivastigmine-containing patch), had a similar maximum value of the drug absorption rate but had a higher cumulative drug permeation amount after 24 hours from the start of the test. This showed that that the preparation of the present invention exhibited a transdermal absorbability superior to that of the commercially available product. In the preparation of Example 5 after 24 hours from the start of the test, no lifting or peeling was observed.

The invention claimed is:

1. A transdermal absorption preparation comprising: an adhesive layer; the adhesive layer comprising:
   5 mass % or more and 30 mass % or less of rivastigmine,
   10 mass % or more and 60 mass % or less of a rubber polymer,
   30 mass % or more and 70 mass % or less of a tackifier resin,
   1 mass % or more and 20 mass % or less of a polymer compound having a nitrogen-containing group, and
   0.1 mass % or more and 6 mass % or less of a cellulose derivative,
   wherein the rubber polymer comprises a liquid polyisoprene rubber and a styrene-isoprene-styrene block copolymer,
   wherein the cellulose derivative is hydroxypropyl methyl cellulose,
   wherein the tackifier resin comprises a hydrogenated rosin glycerol ester, and an alicyclic saturated hydrocarbon resin, and
   wherein the polymer compound having a nitrogen-containing group is a methyl methacrylate-butyl methacrylate-dimethylaminoethyl methacrylate copolymer.

2. The transdermal absorption preparation according to claim 1, wherein the mass ratio of the content of the polymer compound having the nitrogen-containing group to the content of the rivastigmine is 0.05 or more and 4 or less.

* * * * *